(12) United States Patent
Podaima

(10) Patent No.: US 10,987,391 B2
(45) Date of Patent: Apr. 27, 2021

(54) METHOD OF AGGLOMERATING CANNABIS EXTRACT WITH ENERGIZING CONSUMABLES

(71) Applicant: Slate Podaima, Val Caron (CA)

(72) Inventor: Slate Podaima, Val Caron (CA)

(*) Notice: Subject to any disclaimer, the term of this patent is extended or adjusted under 35 U.S.C. 154(b) by 193 days.

(21) Appl. No.: 16/053,328

(22) Filed: Aug. 2, 2018

(65) Prior Publication Data

US 2020/0038465 A1 Feb. 6, 2020

(51) Int. Cl.

| A61K 36/00 | (2006.01) |
|---|---|
| A61K 36/185 | (2006.01) |
| A61K 31/352 | (2006.01) |
| A61K 31/522 | (2006.01) |
| A61K 9/00 | (2006.01) |
| A23G 3/48 | (2006.01) |
| A23G 1/48 | (2006.01) |
| A23L 2/52 | (2006.01) |
| A23L 33/105 | (2016.01) |
| A21D 2/36 | (2006.01) |

(52) U.S. Cl.
CPC .............. *A61K 36/185* (2013.01); *A21D 2/36* (2013.01); *A23G 1/48* (2013.01); *A23G 3/48* (2013.01); *A23L 2/52* (2013.01); *A23L 33/105* (2016.08); *A61K 9/0095* (2013.01); *A61K 31/352* (2013.01); *A61K 31/522* (2013.01); *A23V 2002/00* (2013.01)

(58) Field of Classification Search
None
See application file for complete search history.

(56) References Cited

U.S. PATENT DOCUMENTS

| 8,642,051 | B2 * | 2/2014 | Stillman | A47G 19/2205 424/400 |
|---|---|---|---|---|
| 9,565,865 | B2 | 2/2017 | Bhairam | |
| 9,632,069 | B2 | 4/2017 | Jackson et al. | |
| 2008/0241339 | A1 | 10/2008 | Mitchell et al. | |
| 2012/0043242 | A1 | 2/2012 | Hospodor | |
| 2012/0046351 | A1 | 2/2012 | Hospodor | |
| 2013/0281523 | A1 * | 10/2013 | Letendre | A61K 9/1611 514/454 |
| 2017/0119728 | A1 | 5/2017 | Degeeter | |
| 2017/0196923 | A1 | 7/2017 | Moore | |
| 2017/0340562 | A9 | 11/2017 | Glatzel | |
| 2018/0098552 | A1 * | 4/2018 | Bhairam | A61K 31/352 |
| 2018/0193395 | A1 * | 7/2018 | Epner | A61K 36/258 |
| 2018/0271924 | A1 * | 9/2018 | Kariman | A61K 36/24 |

FOREIGN PATENT DOCUMENTS

| CH | 698251 B1 * | 6/2009 | ............ A23L 13/03 |
|---|---|---|---|
| CN | 105707621 A * | 6/2016 | |
| EP | 3123866 | 2/2017 | |
| WO | 2017180953 | 10/2017 | |

* cited by examiner

*Primary Examiner* — Qiuwen Mi
(74) *Attorney, Agent, or Firm* — Runyan Law; Charles Runyan

(57) ABSTRACT

A method for combining energy supplements such as energy drinks or food items with *Cannabis* extract. The energy supplements include at least one energizing active ingredient of variable potency. The *Cannabis* extract may be produced of variable potency from at least one strain of *Cannabis*. The agglomerated product may be produced in various forms of food or beverages. When used, the agglomerated product may provide the typical effects of *Cannabis* in addition to the added energy and focus provided by energy supplements.

13 Claims, 4 Drawing Sheets

METHOD OF AGGLOMERATING CANNABIS EXTRACT WITH ENERGIZING CONSUMABLES

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of drug, bio-affecting and body treating compositions, and more specifically relates to plant material or plant extract of undetermined constitution as active ingredient (e.g., herbal remedy, herbal extract, powder, oil, etc.).

2. Description of Related Art

Medicinal and recreational use of *Cannabis* is increasing in recent years. One of the effects of *Cannabis* for many users is a significant feeling of being sleepy, tired, or drained of energy. In many cases this feeling is desirable as many people use *Cannabis* for help with sleeping. However, there are many other users who do not want to feel sleepy or tired after using *Cannabis*.

The use of energy supplements such as energy drinks or food items is also increasing in recent years. Many people consume these products to help combat feelings of tiredness and to provide extra energy and focus to stay productive through their day. Many of the people who use energy supplements are also *Cannabis* users. This shared group is lacking in products which combine these substances. A solution is desired.

U.S. Pub. No. 2012/0046351 to Andrew David Hospodor relates to a medicinal *Cannabis* added in food. The described medicinal *Cannabis* added in food includes a product and a process wherein cannabinoids such as Medicinal Δ9-THC and/or other substances associated with medicinal *Cannabis*, including yet not necessarily limited to cannabidiols, cannabigerol are added to a foodstuff where the medicinal *Cannabis* is not evenly distributed throughout the foodstuff where the food stuff contains a known weight of medicinal *Cannabis*. Another provision of the invention is providing controlled amounts or ratios of Δ9-THC as compared to CBD in or on a foodstuff.

BRIEF SUMMARY OF THE INVENTION

In view of the foregoing disadvantages inherent in the known drug, bio-affecting and body treating compositions art, the present disclosure provides a novel method of agglomerating *Cannabis* extract with energizing consumables. The general purpose of the present disclosure, which will be described subsequently in greater detail, is to provide a method for combining energy supplements such as energy drinks or food items with *Cannabis* extract. The energy supplements include at least one energizing active ingredient of variable potency. The *Cannabis* extract may be produced of variable potency from at least one strain of *Cannabis*. The agglomerated product may be produced in various forms of food or beverages. When used, the agglomerated product may provide the typical effects of *Cannabis* in addition to the added energy and focus provided by energy supplements.

A method of combining energizing consumables with *Cannabis* extract is disclosed herein. The method of combining energizing consumables with *Cannabis* extract includes producing consumable foodstuffs which contain an energizing active ingredient; producing *Cannabis* extract containing cannabinoids; and agglomerating the consumable foodstuffs containing at least one energizing active ingredient and *Cannabis* extract containing cannabinoids into a single edible consumable.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a method of agglomerating *Cannabis* extract with energizing consumables, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a drug, bio-affecting and body treating compositions and more particularly to a method of agglomerating *Cannabis* extract with energizing consumables as used to improve the use of plant material or plant extract of undetermined constitution as active ingredient (e.g., herbal remedy, herbal extract, powder, oil, etc.).

Generally, the disclosed invention is a method of infusing caffeine or other stimulants as well as *Cannabis* concentrate into candy, baked goods, and beverages and agglomerating into a food product. The food product created allows a user to experience the effects of *Cannabis*, but without the tired feeling, and can even feel more energetic and focused. The method can use *Cannabis* concentrate from one strain of *Cannabis* or a combination of strains and in different strengths. The caffeine or other stimulants can be used at different strengths and combined with different strengths of *Cannabis* concentrate so that a user can choose their desired combination.

Figure 1:
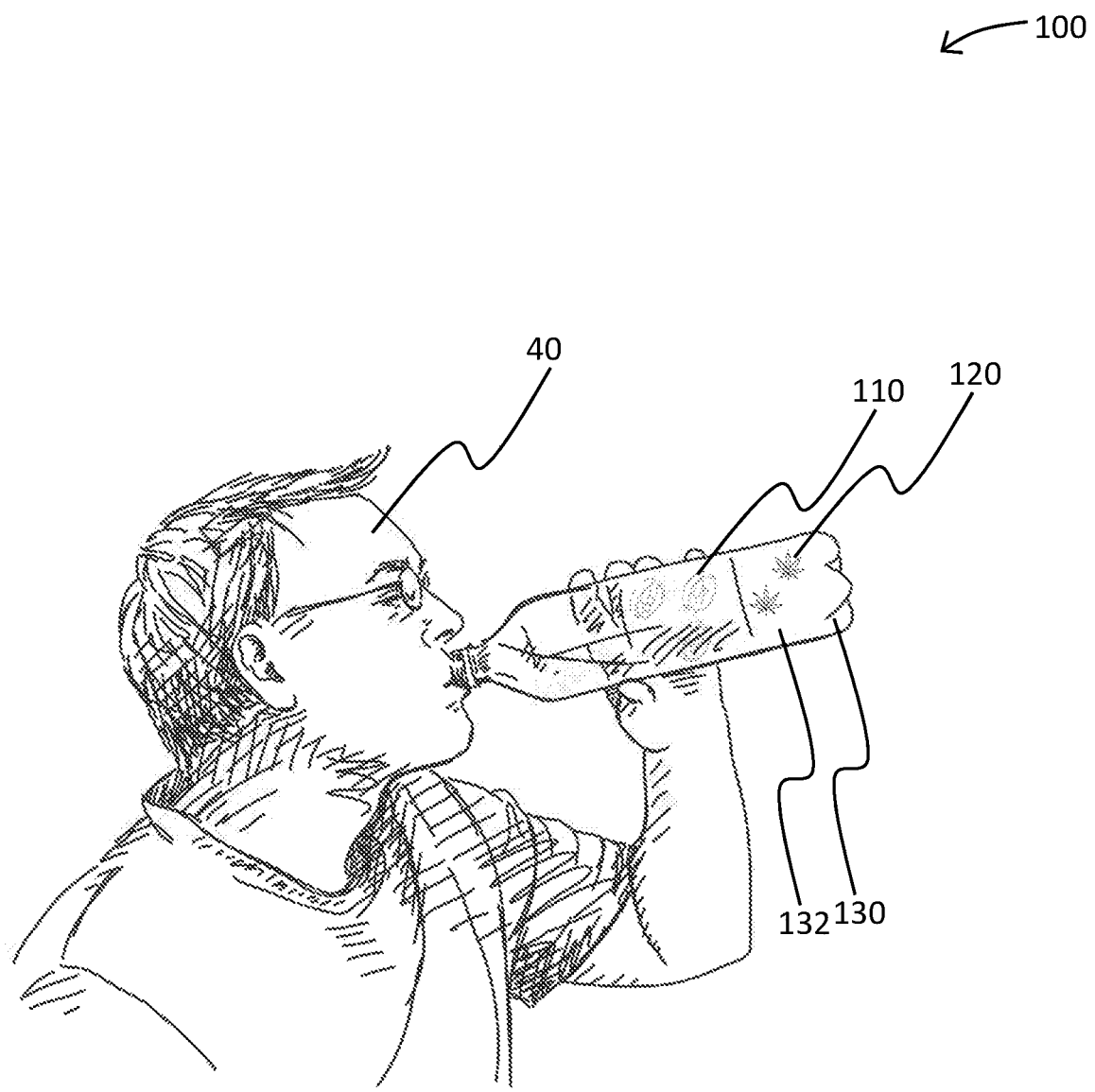
FIG. 1 is a perspective view of the method of combining energizing consumables with *Cannabis* extract during an 'in-use' condition, according to an embodiment of the disclosure.

Referring now more specifically to the drawings by numerals of reference, there is shown in FIGS. 1-4, various views of a method of combining energizing consumables with *Cannabis* extract 100. FIG. 1 shows a method of combining energizing consumables with *Cannabis* extract 100 during an 'in-use' condition 50 by a user 40, according to an embodiment of the present disclosure. As illustrated, the method of combining energizing consumables with *Cannabis* extract 100 may include at least one energizing active ingredient 110, and *Cannabis* extract 120, in the form of an edible consumable 130. The edible consumable 130 displayed is a beverage 132 which is being consumed by a user. The beverage 132 produced using the method 100 may include *Cannabis* extract 120 which was produced from a single particular strain of *Cannabis*. The single particular strain may be an indica-based, a *sativa*-based, or a hybrid-based strain. The *Cannabis* extract 120 included in the beverage 132 may be produced to include no more than 5 mg of tetrahydrocannabinol per serving. The at least one energizing active ingredient 110 may include caffeine, guaranine, *Ginseng*, b-vitamins or taurine, or any combination of these. The at least one energizing active ingredient 110 may be produced synthetically or naturally. The beverage 132 may include no more than 100 mg of caffeine per serving.

According to one embodiment, the method of combining energizing consumables with *Cannabis* extract 100 may be arranged as a kit. The kit may include at least one edible consumable produced using the method of combining energizing consumables with *Cannabis* extract 100 and further comprises a set of instructions. The instructions may detail functional relationships in relation to the method of combining energizing consumables with *Cannabis* extract 100 (such that the method of combining energizing consumables with *Cannabis* extract 100 can be used, maintained, or the like, in a preferred manner).

Figure 2:
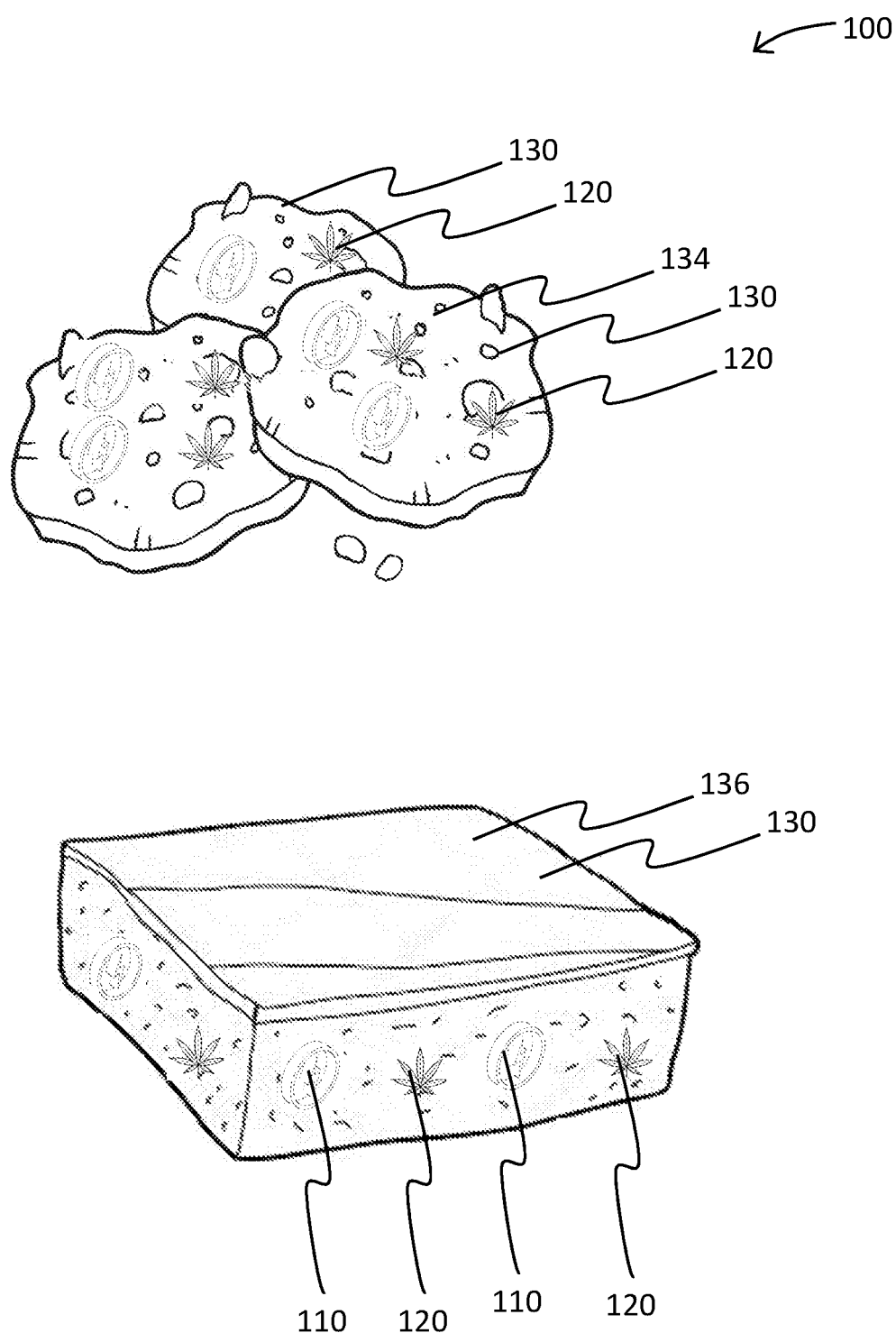
FIG. 2 is a top view of the method of combining energizing consumables with *Cannabis* extract of FIG. 1, according to an embodiment of the present disclosure.

FIG. 2 shows a perspective view of the method of combining energizing consumables with *Cannabis* extract 100 of FIG. 1, according to an embodiment of the present disclosure. As above, the method of combining energizing consumables with *Cannabis* extract 100 may include at least one energizing active ingredient 110, and *Cannabis* extract 120, in the form of an edible consumable 130. The embodiments shown are baked goods 134 including a cookie, a brownie, and a food bar. The at least one energizing active ingredient 110 included in the baked goods 134 is produced with at least 101 mg of caffeine per serving. The *Cannabis* extract 120 included in the baked goods 134 is produced from multiple strains of *Cannabis* and has at least 5.1 mg of tetrahydrocannabinol per serving.

Figure 3:
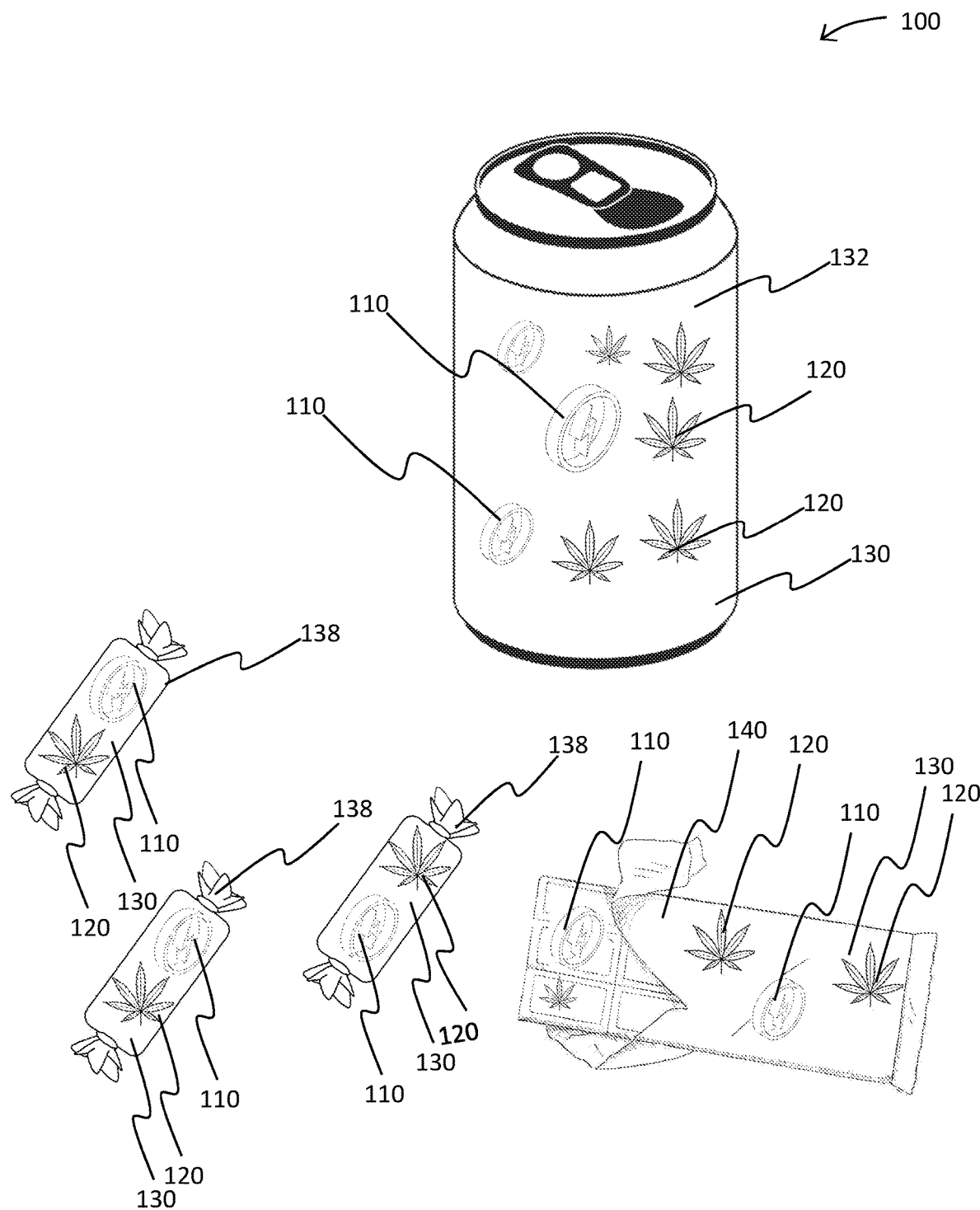
FIG. 3 is a top view of the method of combining energizing consumables with *Cannabis* extract of FIG. 1, according to an embodiment of the present disclosure.

FIG. 3 shows a perspective view of the method of combining energizing consumables with *Cannabis* extract 100 of FIG. 1, according to an embodiment of the present disclosure. As above, the method of combining energizing consumables with *Cannabis* extract 100 may include at least one energizing active ingredient 110, and *Cannabis* extract 120, in the form of an edible consumable 130. The edible consumables 130 shown are a beverage 132, candy and chocolate. The beverage 132, candy and chocolate can include different potencies of *Cannabis* extract 120 and at least one energizing active ingredient 110. This means that based on a consumer's needs or desires, they can choose a product with a more potent or less potent level of *Cannabis* extract 120 and a more potent or less potent level of energizing active ingredient 110.

Figure 4:
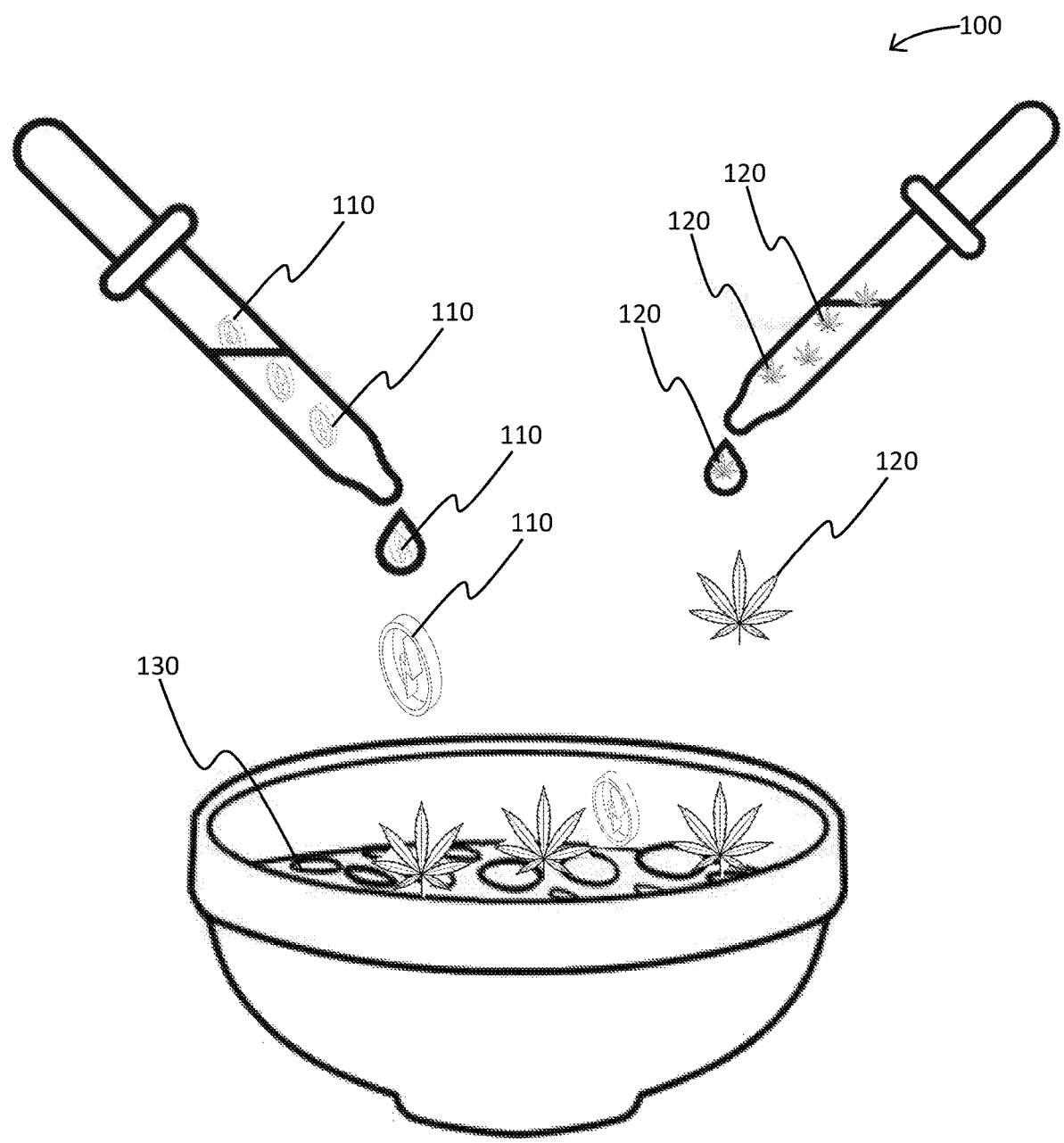
FIG. 4 is a view of the method of use for the method of combining energizing consumables with *Cannabis* extract, according to an embodiment of the present disclosure.

FIG. 4 shows perspective view of the method of combining energizing consumables with *Cannabis* extract 100 of FIG. 1, according to an embodiment of the present disclosure. As above, the method of combining energizing consumables with *Cannabis* extract 100 may include agglomerating at least one energizing active ingredient 110, and *Cannabis* extract 120.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A method of combining energizing consumables with *Cannabis* extract, the method comprising:
   producing consumable foodstuffs which contain an energizing active ingredient;
   producing *Cannabis* extract containing cannabinoids; and
   agglomerating the consumable foodstuffs and the *Cannabis* extract into edible material selected from baked goods, a food bars, or candy,
   wherein the material contains at least 5.1 mg of tetrahydrocannabinol per serving;
   and
   wherein the material contains at least 101 mg of caffeine per serving.

2. The method of claim 1, wherein said *Cannabis* extract is produced from a single particular strain of *Cannabis*.

3. The method of claim 1, wherein said *Cannabis* extract is produced from multiple strains of *Cannabis*.

4. The method of claim 3, wherein said *Cannabis* extract is produced from at least one *sativa*-based strain of *Cannabis*.

5. The method of claim 3, wherein said *Cannabis* extract is produced from at least one indica-based strain of *Cannabis*.

6. The method of claim 3, wherein said *Cannabis* extract is produced from at least one hybrid-based strain of *Cannabis*.

7. The method of claim 6, wherein said at least one energizing active ingredient additionally comprises any one or any combination of guaranine, *Ginseng,* b-vitamins, and taurine.

8. The method of claim 7, wherein said energizing active ingredient is synthetically produced.

9. The method of claim 7, wherein said energizing active ingredient is naturally produced.

10. The method of claim 1, wherein the material is a baked good.

11. The method of claim 1, wherein the material is a candy.

12. The method of claim 10, wherein the material comprises a food bar.

13. A method of combining energizing consumables with *Cannabis* extract, the method comprising:

producing consumable foodstuffs which contain an energizing active ingredient;

producing *Cannabis* extract containing cannabinoids;

agglomerating the consumable foodstuffs and the *Cannabis* extract into edible material selected from baked goods, food bars, or candy, wherein the material contains at least 5.1 mg of tetrahydrocannabinol per serving;

and wherein the material contains at least 101 mg of caffeine per serving and wherein said *Cannabis* extract is produced from at least one hybrid-based strain of *Cannabis*.

\* \* \* \* \*